United States Patent [19]

Pearl, Jr.

[11] Patent Number: 4,664,099

[45] Date of Patent: May 12, 1987

[54] TRACTION DEVICE

[76] Inventor: William J. Pearl, Jr., 925 Mar Vista Ave., Seal Beach, Calif. 90740

[21] Appl. No.: 862,260

[22] Filed: May 12, 1986

[51] Int. Cl.⁴ ............................................. A61F 5/04
[52] U.S. Cl. .................................... 128/75; 128/84 C
[58] Field of Search ................ 128/75, 71, 84 R, 84 C

[56] References Cited

U.S. PATENT DOCUMENTS

| 1,904,942 | 3/1930 | Heigl | 128/84 R |
| 2,053,753 | 9/1936 | Wellington | 128/84 C |
| 2,079,617 | 5/1937 | Johnson | 128/84 C |
| 2,370,251 | 2/1945 | Lewis | 128/84 C |
| 2,373,456 | 4/1945 | Chapman | 128/84 C |
| 2,631,582 | 3/1953 | Bensfield | 128/84 C |
| 2,940,441 | 6/1960 | Demarest et al. | 128/75 |
| 3,134,379 | 5/1964 | Nightingale | 128/75 |
| 3,599,632 | 4/1969 | Childers | 128/25 R |
| 3,662,750 | 5/1972 | Jorgensen | 128/75 |
| 3,827,429 | 8/1974 | Heckers | 128/75 R |
| 4,282,868 | 8/1981 | Riggs | 128/75 |
| 4,323,060 | 5/1982 | Pecheux | 128/84 R |
| 4,621,625 | 11/1986 | Powlan | 128/84 C |

Primary Examiner—Edgar S. Burr
Assistant Examiner—Moshe I. Cohen
Attorney, Agent, or Firm—Howard A. Kenyon

[57] ABSTRACT

A traction device for treating a fracture in the femur bone of a child between the ages of 3 to 10 is described. A special frame and pelvic belt used in conjunction with adjustable tensioning devices is fitted to a child for the treatment of the fracture of the femur bone. This specialized traction device in one embodiment utilizes a pin through the lower part of the femur bone to provide tension to the leg and in another embodiment a leg wrap connected to a sole plate provides tension to the leg. A sling to relieve the downward load of the child patient's leg is provided on one embodiment and there is also provided a leg support under the knee to further relieve the down load resulting from the weight of the leg.

16 Claims, 7 Drawing Figures

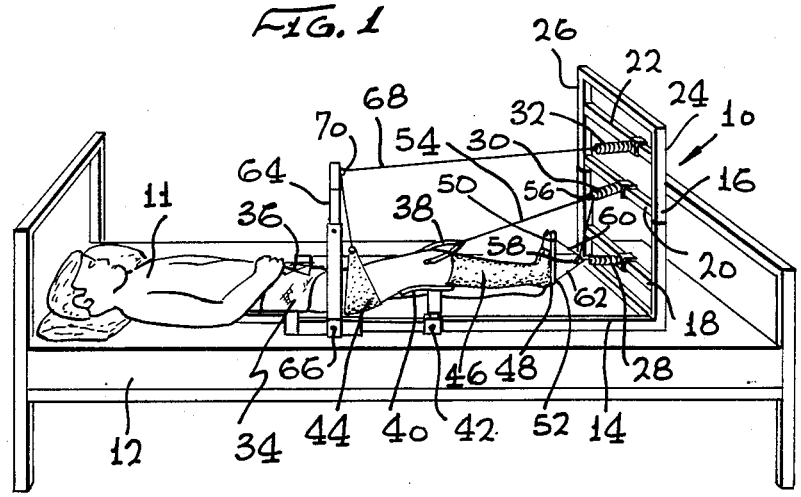
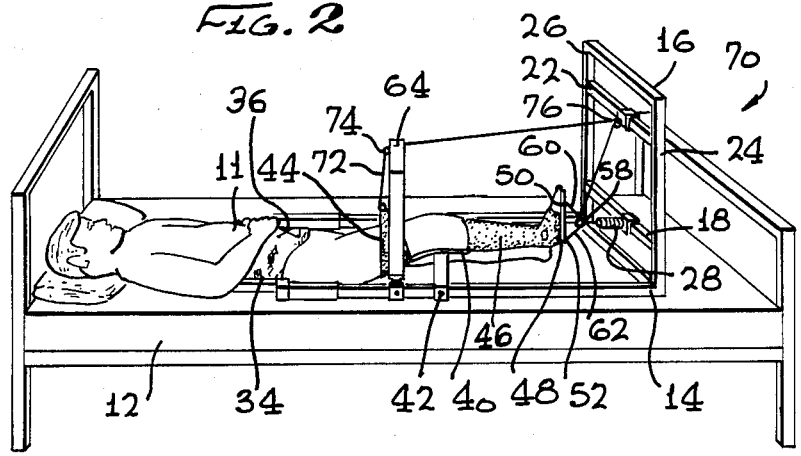
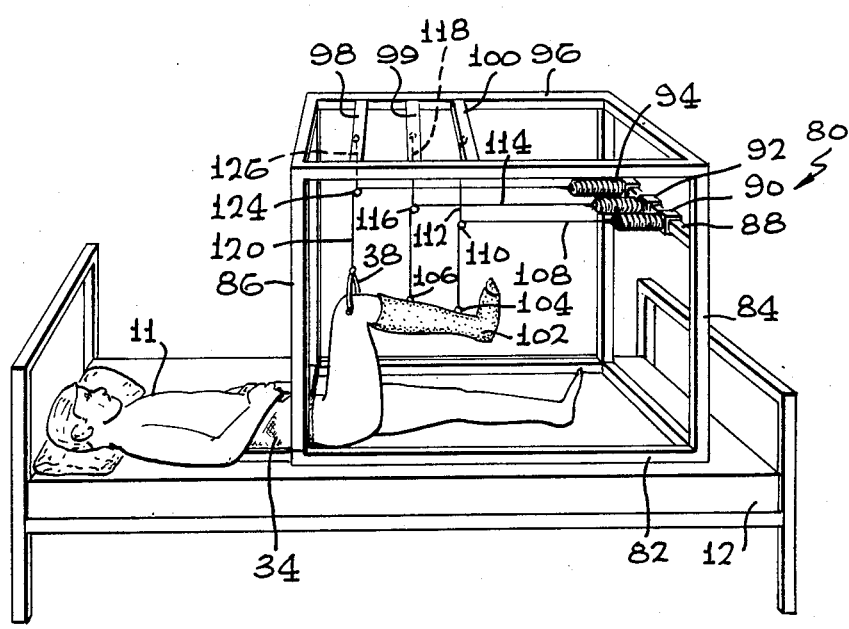

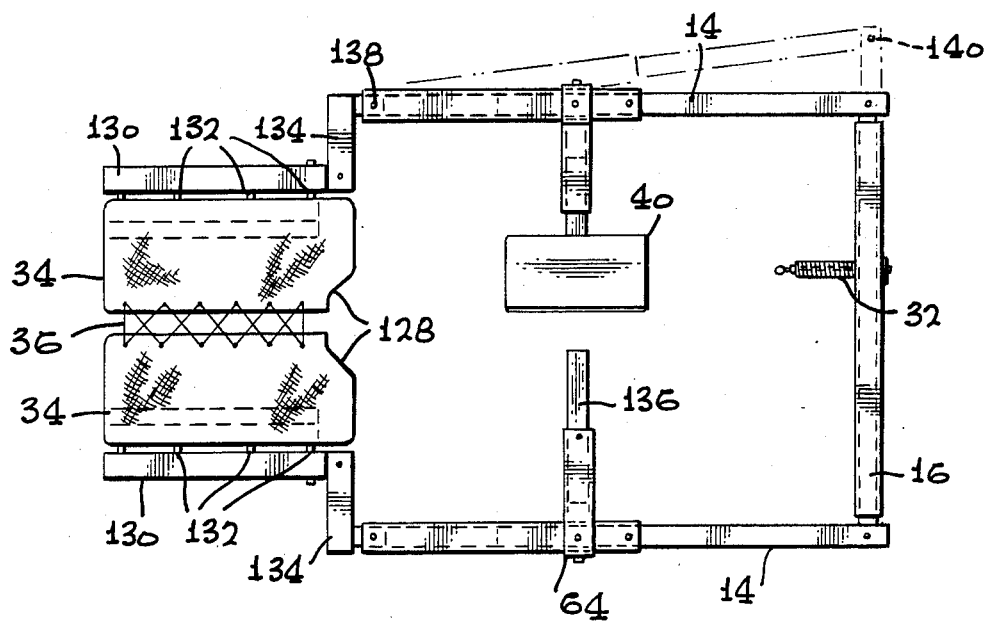
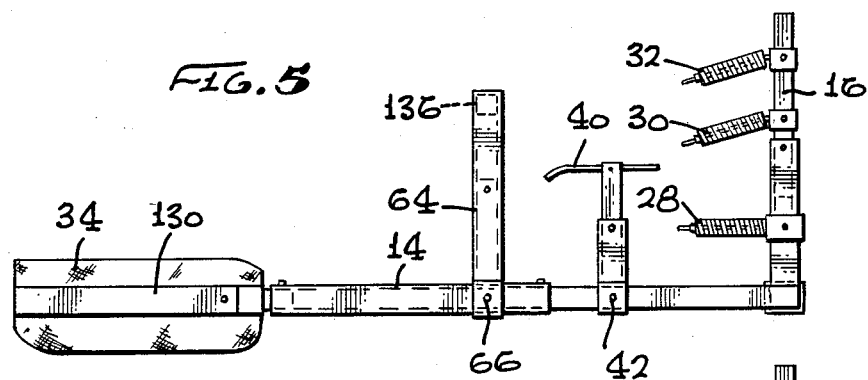
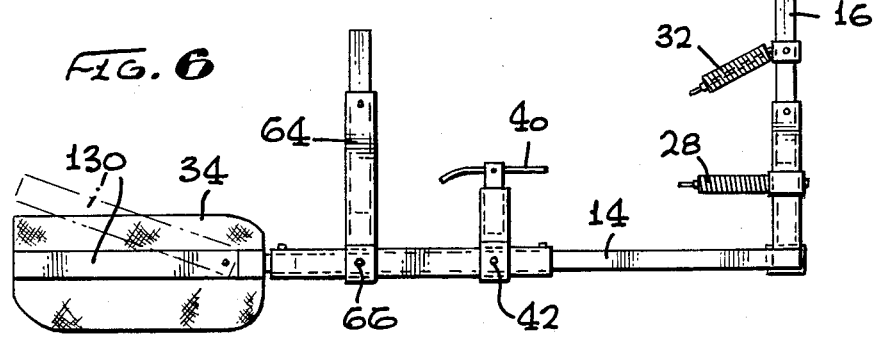
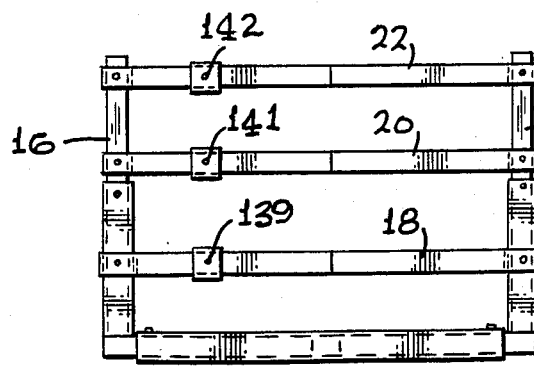

TRACTION DEVICE

BACKGROUND OF THE INVENTION

1. Field of the Invention

This invention relates to a traction device on a child patient and more specifically to a traction device for the fracture of the femur bone while holding the patient in a position that will promote increased healing of the fracture.

2. Description of the Prior Art

Traction devices for applying forces to various portions of the human body for medical treatment have been been long recognized. Many of such structures are bolted to or made a part of a hospital bed or the like. These structures are a maze of pulleys and weights that totally immobolize a patient. For an active child patient, ages 3-10, this type of structure is usually very unsatisfactory as there is considerably more movement with a child confined in a small space than with an adult. In the past, a child is first placed in a "Russells" traction device for a period of 3 to 4 weeks until the fracture is stable with callous then after that the child is put into a one and one-half spica cast for an additional 4 to 5 weeks. A good example of the prior type of structure that is used in treatment of a child patient is in a book entitled Pediatric Orthopedics by W. B. Saunders & Co. FIGS. 8-105 and 8-106.

There are a considerable number of patents utilizing portable traction devices which eliminates the need of bolting the traction structure to a bed and utilizing pulleys and weights. However, most of these are cumbersome and not designed for a child. In addition, many are used as temporary splints while transporting the patient.

One such device is shown in U.S. Pat. No. 3,134,379 to Nightingale. This patent is directed to treatment of a syndetic condition of the lumbar region of the spine.

Another device that provides tracton to the entire body is U.S. Pat. No. 4,282,869 to Riggs. Riggs describes a frame that is pivotable and therefore through lever action, traction may be applied by the patient.

U.S. Pat. No. 4,181,125 to Carlson provides a portable traction device that is used primarily for a patient during transport such as in an ambulance or the like.

U.S. Pat. No. 3,827,429 to Heikes provides a portable traction device for treatment of the spinal column.

U.S. Pat. No. 2,940,441 describes a complex traction device that is motorized so the patient can obtain physical therapeutic treatment in the home by intermittant traction to alleviate intervertebral tension.

U.S. Pat. No. 1,904,942 to Heigh is a device for setting a broken leg by a surgeon single-handed. The device consists of a winch and a rope that stretches the leg so the broken ends can be set.

As can be seen by the above devices none are adaptable to be used by a child who has a fracture of the femur bone. Some of the prior art with pulleys and weights allow the patient to slide on the bed and when the lower limb touches the bed frame, the traction device is no longer functioning. In addition, most of the portable devices are directed to the spinal region which sometimes requires traction for therapeutic relief.

This invention maintains constant traction to the effected femur while freeing nursing personnel of moving and readjusting patient's position in traction. By not losing traction, the healing process is not interrupted by the patient moving towards the bed frame and hence movingthe fractured bone ends which can cause disruption of the healing process. This fraction device will also shorten the time a patient spends in the hospital with a fractured femur bone.

SUMMARY OF THE INVENTION

It is therefore a principal object oftheinvnetion to provide an effective traction device for a child betwen the ages of 3-10.

It is another object of the present invention to provide an effective traction device for a child's femur bone.

It is yet an object of the present invention to provide a traction device that will allow movement of a child while simultaneously keeping tension on the leg.

It is still another object of the present invention to provide a traction device that is portable and can be used when transporting the patient.

Briefly, in accordance with the present invention there is provided a self-contained traction device to treat a simple fracture of the femur bone for a child patient, ages 3-10. The device consists of an adjustable frame with adjustable spring tensioning devices attached to a portion of the frame. A pelvic belt, also attached to the frame, is snugly attached to the patient which prevents the frame from moving upward to the patient's upper part of the body. In one embodiment, a pin through the patient's lower femur bone provides the pulling force needed to keep the femur bone in place during the healing process.

In another embodiment, a leg wrap attached to a sole plate provides the attachment that allows a pulling force required to keep the femur bone in place during the healing process.

These and other objects, features and advantages of the present invention will become more readily apparent upon detailed consideration of the following description of a preferred embodiment with reference to the accompanying drawings.

DESCRIPTION OF THE DRAWINGS

FIG. 1 is a perspective view of one embodiment of the traction device showing a pin through the lower femur bone.

FIG. 2 is a perspective view of a second embodiment of the traction device showing the leg wrap and sole plate.

FIG. 3 is a perspective view of third embodiment of the traction device showing a plaster cast on the tibia and a pin through the lower femur bone.

FIG. 4 shows a top view of the traction device with the various attachments thereof.

FIG. 5 shows a side view of the traction device corresponding to the embodiment shown in FIG. 1.

FIG. 6 shows a side view of the traction device corresponding to the embodiment shown in FIG. 2.

FIG. 7 shows an end view of the vertical frame as shown in FIG. 1.

The novel features which are believed to be characteristic of the invention as to the system together with further objects and advantages thereof, will be better understood from the following description in connection with the accompanying drawings in which the presently preferred embodiments of the invention is illustrated by way of example. It is to be expressly understood, however, that the drawings are for purposes of illustration and description only, and are not intended as a definition of the limits of the invention.

DETAILED DECRIPTION OF THE INVENTION

Referring now to FIG. 1, there is shown a perspective view of the preferred embodiment 10 with a child patient 11 whose lower femur bone has been fractured is in traction on a hospital bed 12. The telescoping parallel tube 14 forming a horizontal frame are on a horizontal surface which in this case in the hospital bed 12. A vertical frame 16 is attached perpendicular to telescoping parallel tubes 14. Telescoping vertical frame 16 has cross members 18, 20 and 22 attached and perpendicular to the side members 24 and 26 of vertical frame 16. The upper portion of side members 24 and 26 telescope into the lower portion and are secured by locking means (not shown). Attached to cross members 18, 20 and 22 are adjustable spring tensioning devices 28, 30 and 32 respectively. A pelvic belt or girdle 34, having a layer of covered sponge rubber attached to the inside thereof, is wrapped around the patient 11 in the pelvic region. Fastening means are shown which in the preferred embodiment is a lacing 36. A pin (not shown) is placed in the lower part of the femur bone so that the ends of the pin are connected to a stirrup 38. A telesocping leg support 40 is adjusted by telescoping means to provide comfortable vertical support to the leg. The telescoping leg support 40 is also adjusted longitudinally along tube 14 until it is in the proper and comfortable place for support. Locking means 42 is then provided to lock the longitudinal movement of leg support 40. A flexible sling 44 is placed in FIG. 1 under the upper region of the femur bone to aid in the support of the child patient's leg. A leg wrap 46 is snugly placed around the child patient's leg and further attached to a sole plate 48. Sole plate 48 has two attachments 50 and 52 fastened on the bottom thereto. A cable 54 is fastened to stirrup 38 passing through pulley 56 which is attached to adjustable spring tensioning means 30 and further through pulley 58 terminating at adjustable spring tensioning means 28. Short cables 60 and 62 fasten pulley 58 to attachments 50 and 52 to the bottom of sole plate 48. A telescoping post 64 is attached to the tube 14 and is longitudinally adjustable along tube 14. Locking means 66 holds the telesocping post 64 firmly in place on tube 14. Cable 68 is attached to flexible sling 44 and passes through pulley 70 on an overhanging member (not shown in FIG. 1.) Cable 68 is further attached to adjustable spring attaching means 32. Cables 54 and 68 also have adjusting means (not shown) to adjust the length of the cables relative to the size of the patient. All of the telescoping tubes in FIG. 1 have locking means not shown to prevent movement after the desired dimension is set.

Turning now to FIG. 2 generally shown as 70 there is seen a child patient 11 who has a fracture of the femur bone and is lying on hospital bed 12 with pelvic belt 34 containing lacing 36. Horizontal telescoping tubes 14 forming a horizontal frame lie on a horizontal surface which in this case is hospital bed 12. A vertical frame 16 is mounted perpendicular to horizontal telescoping tubes 14. In this embodiment, only horizontal members 18 and 22 are attached and are perpendicular to side members 24 and 26 of vertical frame 16. In addition only one adjustable spring tensioning means 28 is used to provide a pull on the fractured leg. As is noted, leg wrap 46 is tied to sole plate 48. Sole plate 48 has attachments 50 and 52 that have short cables 60 and 62 terminating at connection 58. In this embodiment, patient 11 has the sling 44 at the lower part of the femur bone since there is no pin through the bone. A telescoping post 64 is attached to tube 14 and can be adjusted longitudinally along tube 14. Locking means 42 in the longitudinal directiOn is provided for the leg support 40. A cable 72 is attached to sling 44 and passes through a pulley 74 attached to the overhanging member (not shown in FIG. 2) of post 64, thereafter passing through pulley 76 attached to cross member 22. The cable 72 then passes through pulley 58 and terminates at the adjustable spring tension means 28. Cable 72 has an adjusting means (not shown) to adjust the length of the cable relative to the size of the patient. All of the telescoping tubes in FIG. 2 have locking means not shown to prevent movement after the desired dimension is set.

Turning now to FIG. 3, generally shown at 80, there is shown a modification of the basic traction device as shown in FIGS. 1 and 2 wherein there is a horizontal tube 82 lying on a hospital bed 12. A child patient 11 whose femur bone is fractured is also lying on hospital bed 12. A first vertical frame 84 is attached at the bottom to one end and perpendicular to horizontal frame 82. A second vertical frame 86 is attached at the bottom to the other end of horizontal frame 82 and perpendicular to horizontal frame 82. Vertical frame 84 has attached a cross member 88 that further has three adjustable spring tensioning means 90, 92 and 94 attached thereto. Vertical frames 84 and 86 have a horizontal frame 96 joining the top ends of frames 84 and 86. Frame 96 has cross members 98, 99 and 100 firmly attached thereto to the sides of frame 96. A pelvic belt 34 with the adjoining members as described in FIG. 4 is attached to frame 82. A pin (not shown) is placed through the lower femur bone with stirrup 38 attached to the ends of the pin. In this embodiment a plaster cast 102 has been placed on the lower leg with attachments 104 and 106 imbedded into the plaster. This embodiment has three cables that assist in providing the traction on the femur bone. Cable 108 is attached to the lower fitting 104 in the plaster cast 102 and passes through pulley 110 which is attached by a short cable 112 to cross member 100. Cable 108 terminates at the adjustable spring tensioning means 90. Cable 114 is attached to the upper fitting 106 in the plaster cast 102 and passes through pulley 116 which is attached by a short cable 118 to cross member 99. Cable 114 terminates at the adjustable spring tensioning means 92. Cable 120 which provides the most tension of the femur bone is attached to a stirrup 38 and passes through pulley 124 which is attached by a short cable 126 fastened to cross member 98. Cable 120 terminates at the adjustable spring tensioning means 94.

FIG. 4 shows a top view presenting the basic components of the preferred embodiment of the present invention. There is seen the telescoping parallel tubes 14 and the top of vertical frame 16. Cross members 18, 20 and 22 as shown in FIG. 1 are hidden from view. An adjustable spring tensioning means 32 as seen in FIG. 1 is shown attached to cross member 18. Pelvic girdle 34 with lacing 36 is clearly shown in this view. Also cutouts 128, back and front of the pelvic belt, helps the patient eliminate waste. The pelvic belt 34 is attached to one leg 130 of an L shaped member at 132. Another leg of the L shaped member 134 attaches member 130 to horizontal member 14. Vertical telescoping post 64 is shown with overhanging members 136. Telesocping leg support 40 is shown in FIG. 4 being opposite the vertical post 64 for clarity where, in reality, both 64 nd 40 would be located on tube 14 on the same side. This view also shows how tube 14 pivots at 138 and 140 to allow telescoping of tube 14 into the bottom member of vertical frame 16.

FIG. 5 shows a side view of the preferred embodiment and the adjustable spring tensioning means 28, 30 and 32. Telescoping horizontal frames 14 and vertical frame 16 can also be seen in this view. Telescoping vertical post 64 is shown slideably attached to tube member 14. Locking means 66 for telesocping vertical post 64 is also seen in this view. The telescoping leg support 40 as shown in FIG. 1 is shown with locking means 42. The leg 130 of L shaped member that is attached to the pelvic girdle 34 is presented as a side view.

FIG. 6 is another side view of the preferred embodiment showing adjustable spring tensioning means 28 and 32, horizontal tube 14 telescoping vertical frame 16, vertical telescoping post 64, telescoping leg support 40 and one leg 130 of L shaped members. This view shows how leg 130 may pivot upward to allow the patient to obtain a more comfortable position in the hospital bed 12.

FIG. 7 shows a front view of telescoping vertical frame 16 with cross members 18, 20 and 22. The attachments of adjustable spring tensioning means as described in the present invention can be moved longitudinally and secured by locking means 139, 141 and 142. The adjusting means of the spring tensioning means is a threaded rod (not shown) that will put more or less initial tension on the spring when the threaded rod is turned in the spring holder. A spring adjustment of 1 to 15 pounds is used in the present invention.

All of the tubing in the present invention is thick wall, square aluminum tubing to facilitate the sliding members moving longitudinally and prevent rotation of the accessories.

Accordingly, there has been provided in accordance with the invention a traction device that fully satisfies the objectives set forth above. It is understood that all terms used herein are descriptive rather than limiting. While the invention has been described in conjunction with specific embodiments. It is evident that many alternatives, modifications, and variations will be apparent to those skilled in the art in light of the disclosure herein. Accordingly, it is intended to include all such alternatives, modifications, and variations that are within the spirit and scope of the appended claim.

What is claimed is:

1. A traction device for the treatment of a fracture of the femur bone in the leg of a child patient comprising:
   a frame, placed on a horizontal surface, said frame being formed by a pair of parallel telescoping tubes having a first and second end on each tube;
   an L shaped member attached to and being a projection from said first end of each of said telescoping tubes;
   a vertical frame attached to said second end of said tubes with at least one cross member;
   a telescoping L shaped post attached to said telescoping tubes perpendicular to said frame with a member perpendicular to said post and overhanging said child patient's leg;
   a leg sling attached to said member perpendicular to said post overhanging said child patient's leg;
   at least one adjustable tensioning means attached to said cross member of said vertical frame;
   a pelvic girdle disposed to wrap around said child patient in the pelvic region and further attached to said L shaped member on each side of said pelvic girdle;
   a flexible wrap placed snugly around a child patient's lower leg, said wrap being further attached to a sole plate on a child patient's foot;
   a pin through the lower end of said femur bone, the ends of said pin attached to a stirup;
   a telescoping leg support attached and adjustable longitudinally along one of said parallel telescoping tubes;
   a first cable attached to said stirrup and further attached by a first pulley to a first adjustable tensioning means attached to a first cross member, said cable further attached by a second pulley to a second adjustable tensioning means attached to a second cross member, with said second pulley terminating at a cable attachment on said sole plate which is thereby attached to said flexible wrap;
   a second cable attached to said sling and further attached to a third pulley, said third pulley being attached to said overhanging member on said telescoping L shaped post, said second cable terminating on the end of a third adjustable tensioning means attached to a third cross member;
   adjusting means on said first and said second cables in combination with adjustable tensioning means to provide the required tension on said child patient's leg.

2. A traction device as described in claim 1 wherein said pelvic belt has a layer of covered sponge rubber attached to the inside of said belt.

3. A traction device as described in claim 1 wherein said L shaped member attached to said pelvic belt is pivotally upward.

4. A traction device as described in claim 1 wherein said telescoping tubes pivot horizontally at said first end and said second end of said telescoping tubes telescope horizontally into the bottom member of said vertical frame.

5. A traction device as described in claim 1 wherein said device is for a child between the ages of 3 and 10.

6. A traction device for the treatment of a fracture of the femur bone in the leg of a child patient comprising:
   a frame, placed on a horizontal surface, said frame being formed by a pair of parallel telescoping tubes having a first and second end on each tube;
   an L shaped member attached to and being a projection from said first end of each of said telescoping tubes;
   a vertical frame attached to said second end of said tubes with at least one cross member;
   a telescoping L shaped post attached to said telescoping tubes perpendicular to said frame with a member perpendicular to said post and overhanging said child patient's leg;
   a leg sling attached to said member perpendicular to said post overhanging said child patient's leg;
   at least one adjustable tensioning means attached to said cross member of said vertical frame;
   a pelvic girdle disposed to wrap around said child patient in the pelvic region and further attached to said L shaped member on each side of said plastic girdle;
   a flexibile wrap snugly around said child patient's lower leg, said wrap being further attached to a sole plate on a child patient's foot;

a cable attached to said sling and further attached to a first pulley, said first pulley being attached to said overhanging members on said telescoping L shaped post, said cable further attached to a second pulley on a first cross member, said cable also being threaded through a third pulley, said third pulley being attached to said cable attachment on said sole plate which is thereby attached to said flexible wrap, said cable terminating at an adjustable tensioning means attached to a second cross member;

adjusting means on said third cable in combination with adjustable tensioning means to provide the required tension on said child patient's leg.

7. A traction device for the treatment of a fracture of the femur bone in the leg of a child patient comprising:
   a frame having a first and a second end and formed by a pair of parallel telescoping tubes placed on a horizontal surface;
   a first vertical frame attached to the first end of said tubes;
   a second vertical frame attached to the second end of said tubes, having at last one cross member;
   an upper frame connecting the top of said first vertical frame to the top of said second vertical frame, said upper frame having at least two cross members;
   a pin through said child patient's lower femur bone, said pin ends connected to a stirrup;
   a plaster cast covering the lower tibia region, said cast having two spaced apart attachments in the shin region;
   a pelvic belt attached to said child patient, said pelvic belt further attached to an L shaped extension of said first end of said frame formed by said parallel tubes;
   at least one adjustable tensioning means attached to said cross members on said second vertical frame;
   a first cable attached to the first of said attachments on said cast and further passing through a fist pulley attached to the first of said cross members on said upper frame and terminating at a first adjustable tensioning means attached to a cross member;
   a second cable attached to the second of said attachments on said cast and further passing through a second pulley attached to said second cross member on said upper frame and terminating at a second adjustable tensioning means attached to said cross member;
   a third cable attached to said stirrup and further passing through a third pulley attached to said third cross member on said upper frame and terminating at a third adjustable tensioning means attached to said cross member.

8. The first, second and third cables as described in claim 7 wherein said cables have a cable tension adjusting means in conjunction with said adjustable tensioning mechanisms whereby the correct pull may be applied and provide the correct amount of tension in the fractured leg of said patient.

9. A traction device as described in claim 7 where said pelvic belt has a layer of covered sponge rubber attached to the inside of said belt.

10. A traction device for the treatment of a fracture of the femur bone in the leg of a child patient comprising:
   a frame, placed on a horizontal surface, said frame formed by a pair of parallel telescoping tubes, generally spaced apart, having a first and second end;
   an L shaped member being a projection of each of the first end said tubes, said L shaped member having a first and second leg, said first end of said parallel tubes being normal to and and pivotally attached to one end of said first legs of said L shaped member, the other end of said first legs of said L shaped member being disposed in a hinge relationship with said second legs of said L shaped member, said second legs of said L shaped member extending perpendicular to said first leg;
   a vertical frame having an upper and lower end, said vertical frame being perpendicular to said horizontal frame, said vertical frame lower end having a lower member disposed in telescoping relationship with a hinged member on the second end of said parallel telescoping tubes, said vertical frame having two telescoping vertical end members with at least one horizontal cross member normal to said end members and attached to said end members, one horizontal cross member attached to the lower telescoping part of said vertical end members and the other horizontal cross members attached to the upper telescoping part of said end members;
   an L shaped telescoping post perpendicular to said frame and attached to one of said parallel telescoping tubes, said telescoping post having a perpendicular member overhanging said child patient's leg;
   a telescoping leg support attached and adjustable longitudinally along one of said parallel telescoping tubes;
   at least one adjustable spring tensioning means attached to and longitudinally adjustable on said cross members of said vertical frame;
   locking means for locking each telesocping tube and each attachment in place;
   a pelvic girdle disposed to snugly wrap around said child patient in the pelvic region and further attached on the side of said child patient to said second leg of said L shaped member on each side of said pelvic gidle;
   a wrap snugly around said child patient's leg in the lower tibia region, said wrap extending around said child patient's ankles and further attached to a foot sole plate, said sole plate containing cable attaching means;
   a pin through the lower end of said femur bone, the end of said pin attached to a stirrup;
   a flexible sling fitted under the upper portion of said child patient's femur bone region;
   a first cable attached to said stirrup and further attached by a first pulley to a first adjustable tensioning means attached to a first cross member, said cable further attached by a second pulley to a second adjustable tensioning means attached to a second cross member, said second pulley terminating at a cable attachment on said sole plate which is thereby attached to said flexible wrap;
   a second cable attached to said sling and further attached to a third pulley which is attached to said overhanging member on said post, said second cable terminating on the end of a third adjustable tensioning means attached to a third cross member;
   adjusting means in said cables whereby said cables may be made shorter or longer to apply the required amount of spring tension supplied by said adjustable spring tensioning means and therefore keep constant traction on the fracture of the femur bone.

11. A traction device as described in claim 10 wherein said flexible sling is made of soft fabric.

12. A traction device as described in claim 10 wherein said pelvic belt has a layer of covered sponge rubber attached to the inside of said belt.

13. A traction device as described in claim 10 wherein said pelvic wrap is flexible and stretchable.

14. A traction device as described in claim 10 wherein said pelvic belt is designed in the front and back to allow said patient to dispose of human waste.

15. A traction device as described in claim 10 wherein said device is for a child between the ages of 3 and 10.

16. A method for the treatment of a fracture of the femur bone in the leg of a child patient comprising:
   providing a frame, placed on a horizontal surface, said frame formed by a pair of parallel telescoping tubes, generally spaced apart, having a first and second end;
   providing an L shaped member being a projection of each of the first end said tubes, said L shaped member having a first and second leg, said first end of said parallel tubes being normal to and and pivotally attached to one end of said first legs of said L shaped member, the other end of said first legs of said L shaped member being disposed in a hinge relationship with said second legs of said L shaped member, said second legs of said L shaped member extending perpendicular to said first leg;
   providing a vertical frame having an upper and lower end, said vertical frame being perpendicular to said horizontal frame, said vertical frame lower end having a lower member disposed in telescoping relationship with a hinged member on the second end of said parallel telescoping tubes, said vertical frame having two telescoping vertical end members with at least one horizontal cross member normal to said end members and attached to said end members, one horizontal cross member attached to the lower telescoping part of said vertical end members and the other horizontal cross members attached to the upper telescoping part of said end members;
   providing an L shaped telescoping post perpendicular to said frame and attached to one of said parallel telescoping tubes, said telescoping post having a perpendicular member overhanging said child patient's leg;
   providing a telescoping leg support attached and adjustable longitudinally along one of said parallel telescoping tubes;
   attaching at least one longitudinally adjustable spring tensioning means to said cross members of said vertical frame;
   providing locking means for locking each telescoping tube and each attachment in place;
   providing a pelvic girdle disposed to snugly wrap around said patient in the pelvic region and further attached on the side of said child patient to said second leg of said L shaped member on each side of said pelvic girdle;
   providing a wrap snugly around said child patient's leg in the lower tibia region, said wrap extending around said child patient's ankles and further attached to a foot sole plate, said sole plate containing cable attaching means;
   providing a pin through the lower end of said femur bone, the end of said pin attached to a stirrup;
   providing a flexible sling fitted under the upper portion of said child patient's femur bone region;
   attaching a first cable to said stirrup and further attached by a first pulley to a first adjustable tensioning means attached to a first cross member, said cable further attached by a second pulley to a second adjustable tensioning means attached to a second cross member, said second pulley terminating at a cable attachment on said sole plate which is thereby attached to said flexible wrap;
   attaching a second cable to said sling and further attached to a third pulley which is attached to said overhanging member on said post, said second cable terminating on the end of a third adjustable tensioning means attached to a third cross member;
   providing adjusting means in said cables whereby said cables may be made shorter or longer to apply the required amount of spring tension supplied by said adjustable spring tensioning means and therefore keep constant traction on the fracture of the femur bone.

* * * * *